United States Patent [19]

Leary et al.

[11] Patent Number: 5,197,597

[45] Date of Patent: * Mar. 30, 1993

[54] SUTURE RETAINER

[75] Inventors: Craig W. Leary, Bridgeport; Christopher M. Scanlon, Milford, both of Conn.

[73] Assignee: United States Surgical Corporation, Norwalk, Conn.

[ * ] Notice: The portion of the term of this patent subsequent to Mar. 3, 2009 has been disclaimed.

[21] Appl. No.: 821,002

[22] Filed: Jan. 15, 1992

Related U.S. Application Data

[63] Continuation-in-part of Ser. No. 533,461, Jun. 5, 1990, Pat. No. 5,092,455.

[51] Int. Cl.$^5$ ............................................. A61B 17/06
[52] U.S. Cl. .................... 206/63.3; 206/482; 206/483; 206/495
[58] Field of Search ................ 206/63.3, 63.5, 482, 206/483, 495, 339

[56] References Cited

U.S. PATENT DOCUMENTS

| | | | |
|---|---|---|---|
| 2,938,624 | 5/1960 | Runkel et al. | 206/63.3 |
| 3,136,418 | 6/1964 | Stacy et al. | 206/63.3 |
| 3,162,307 | 12/1964 | Regan, Jr. . | |
| 3,206,018 | 9/1965 | Lewis et al. | 206/63.3 |
| 3,280,971 | 10/1966 | Regan, Jr. | 206/63.3 |
| 3,627,120 | 12/1971 | Bordeau | 206/63.3 X |
| 3,727,658 | 4/1973 | Eldridge, Jr. . | |
| 3,759,376 | 9/1973 | Lisowski . | |
| 3,779,375 | 12/1973 | Foster | 206/63.3 |
| 3,857,484 | 12/1974 | Thyen . | |
| 3,972,418 | 8/1976 | Schuler et al. . | |
| 3,985,227 | 10/1976 | Thyen et al. | 206/63.3 |
| 4,121,711 | 10/1978 | Bolanowski | 206/63.3 |
| 4,135,623 | 1/1979 | Thyen . | |
| 4,183,431 | 1/1980 | Schmidt et al. | 206/63.3 |
| 4,391,365 | 7/1983 | Batchelor . | |
| 4,422,552 | 12/1983 | Palmer et al. | 206/482 X |
| 4,424,898 | 1/1984 | Thyen et al. | 206/63.3 |
| 4,572,363 | 2/1986 | Alpern . | |
| 4,574,948 | 3/1986 | Huck et al. | 206/63.3 |
| 4,700,833 | 10/1987 | Smith | 206/380 |
| 4,700,843 | 10/1987 | Smith . | |
| 4,896,767 | 2/1989 | Pinheiro . | |
| 5,092,455 | 3/1992 | Leary | 206/63.3 |

FOREIGN PATENT DOCUMENTS

| | | |
|---|---|---|
| 617691 | 4/1961 | Canada . |
| 650778 | 10/1962 | Canada . |
| 662417 | 4/1963 | Canada . |
| 0208542 | 1/1987 | European Pat. Off. . |
| 6502090 | 8/1965 | Netherlands . |
| 6504467 | 10/1966 | Netherlands . |
| 736038 | 3/1955 | United Kingdom . |
| 1081123 | 8/1967 | United Kingdom . |

*Primary Examiner*—Paul T. Sewell
*Assistant Examiner*—Jacob K. Ackun, Jr.
*Attorney, Agent, or Firm*—Thomas R. Bremer; Peter G. Dilworth; Rocco S. Barrese

[57] ABSTRACT

A suture retainer is provided with an arrangement of suture-retaining tabs of complex configuration and needle-retaining tabs of a number and distribution which enable the retainer to accommodate any one of several types of combined surgical suture-needle devices.

15 Claims, 7 Drawing Sheets

SUTURE RETAINER

CROSS REFERENCE TO RELATED APPLICATION

The present application is a continuation-in-part of commonly assigned, copending U.S. patent application Ser. No. 07/533,461 filed Jun. 5, 1990 and now U.S. Pat. No. 5,0924,55.

BACKGROUND OF THE INVENTION

This invention relates to the packaging of surgical sutures and, in particular, to a retainer card for accommodating one or more suture products, e.g., a combined surgical suture-needle device, also commonly referred to as an "armed suture", or merely "a suture", as part of a suture package.

Retainers for surgical sutures are constructed according to the nature of the suture and its intended use. There are many sizes of sutures and many materials of construction such as cotton, silk, stainless steel, and braided wire. There are also several types of needles including those of straight and curved configuration. The ideal suture package protects the suture during shipping and handling, accommodates a variety of suture and needle constructions and affords easy removability of the suture-needle device(s) therefrom.

There exists many packaging arrangements for suture-needle devices. However, for the most part, these packages have been designed to accommodate a specific suture-needle configuration. That is, the package may be designed to accommodate a long straight needle or a curved needle but not both. Many packages have been developed for use with single-armed sutures, for example, a suture having a needle at one end. Packages also exist for accommodating double armed sutures, i.e., sutures possessing needles at both ends. There are also several different types of packages containing a plurality of sutures and designed in such a way as to allow all of the sutures to be removed from the package at once or one at a time.

Illustrative of known types of suture retainers are those disclosed in U.S. Pat. Nos. 3,206,018; 4,391,365; 4,572,363; and 4,700,833. The last mentioned of these disclosures, U.S. Pat. No. 4,700,833, describes a suture retainer, or winding card, possessing a base panel and several flaps which extend from, and fold over, the base panel to cover and secure a suture or combined suture-needle device disposed thereon. A number of die-cut U-shaped tabs are arranged along the periphery of the base, the convex portion the tabs being oriented toward the edges of the panel and away from its center. By slightly displacing the tabs from the plane of the base panel, the tabs may serve to receive a coiled length of suture. The base panel also possesses a pair of opposed D-shaped apertures for receiving a pin around which a suture may be wound, e.g., in a figure eight pattern, to facilitate an alternative suture-packaging operation.

SUMMARY OF THE INVENTION

It is an object of the invention to provide a suture retainer comprising a base panel possessing a plurality of spaced-apart suture-engaging tabs of compound configuration defined thereon and a plurality of spaced-apart needle-engaging tabs defined upon the base panel, the number and distribution of the needle-engaging tabs being such as to accommodate a variety of needle sizes and/or configurations.

It is a particular object of the invention to provide a suture retainer which, in its packaged and sealed configuration, exhibits a narrower profile for a given type and quantity of sutures than that of the known type of retainers, e.g., as described in U.S. Pat. No. 4,700,833 discussed above.

It is another object of the invention to provide a suture retainer which accommodates a wide variety of sutures and/or combined suture-needle devices such that the number of retainers which must be manufactured and inventoried to meet the packaging needs of a comprehensive line of suture products is kept to a minimum.

In keeping with these and other objects of the invention, there is provided a suture retainer comprising a base panel possessing a plurality of suture-engaging spaced apart tabs of compound configuration defined thereon and a plurality of spaced-apart needle-engaging tabs defined upon the base panel, said tabs being of sufficient number and distribution to accommodate a plurality of needle sizes and/or configurations.

The expression "compound configuration" as applied to the suture-engaging tabs of the retainer herein shall be understood to define such a tab having at least one pair of opposed elements with one element of the pair being elevated above, and the other element of the pair being depressed below, the plane of the base panel in the packaged condition of the suture retainer.

Compared with the generally U-shaped suture-engaging tabs of the retainer described in aforementioned U.S. Pat. No. 4,700,833, the suture-engaging tabs of the retainer of this invention, due to their compound configuration, result in a narrower packaging profile.

In addition, the provision of needle-engaging tabs upon the base panel of the suture retainer herein, a feature which is lacking in the retainer of U.S. Pat. No. 4,700,833, makes it possible for the retainer of this invention to accommodate a variety of different sizes and/or shapes of surgical needles. It is therefore possible to employ one or at most very few retainer configurations to meet the packaging needs of an entire line of suture products.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENT

Figure 1:
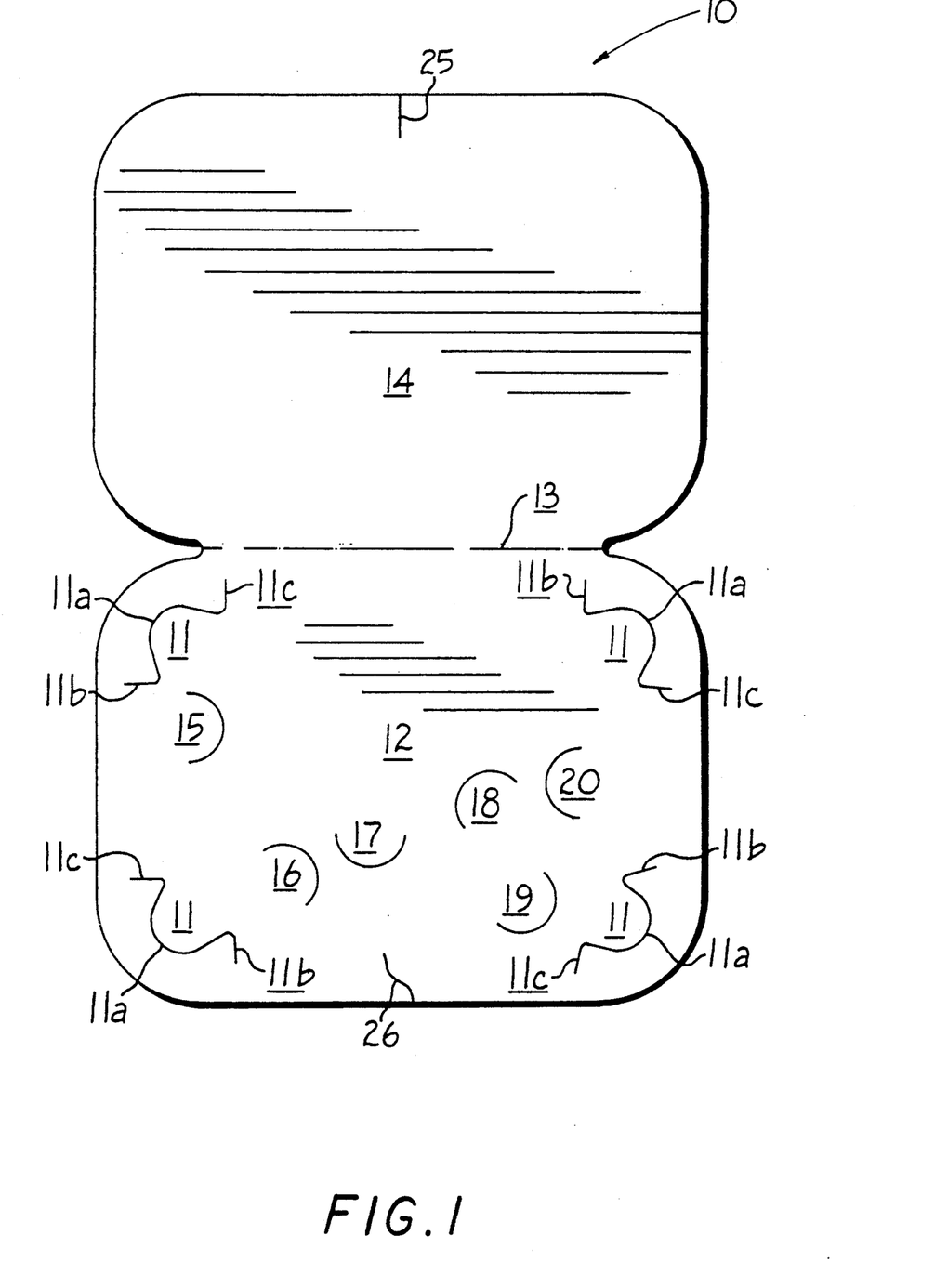
FIG. 1 is a plan view of one embodiment of a suture retainer in accordance with this invention shown in the fully open condition.

Referring initially to FIG. 1, there is illustrated a suture retainer 10 possessing a base panel 12 of rectangular (square) shape and an optional cover panel 14 attached to base panel 12 along common edge 13 advantageously defined by a fold line or crease which facilitates the folding over of the cover panel upon the base panel in the packaged condition of the retainer.

Figure 2:
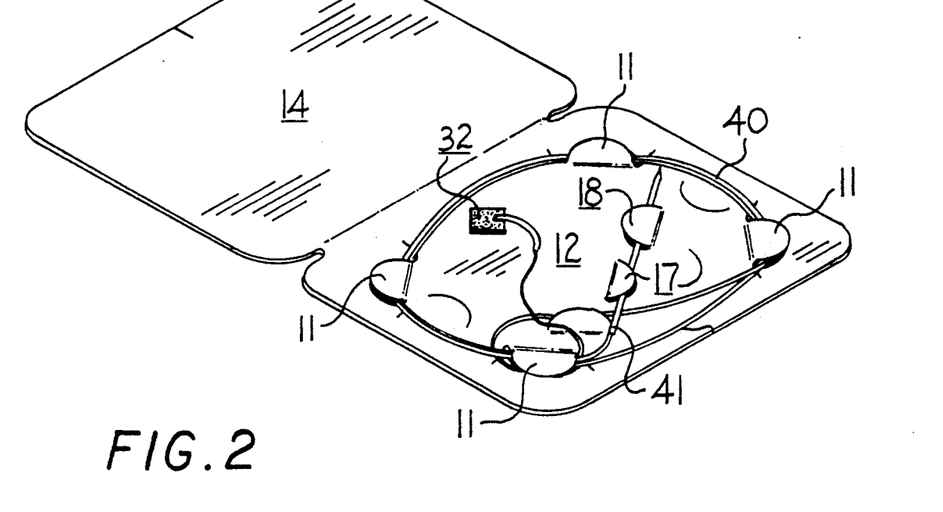
FIG. 2 is a perspective view of the suture retainer of FIG. 1 loaded with a combined surgical suture-needle device and shown in the open condition.
Figure 6:
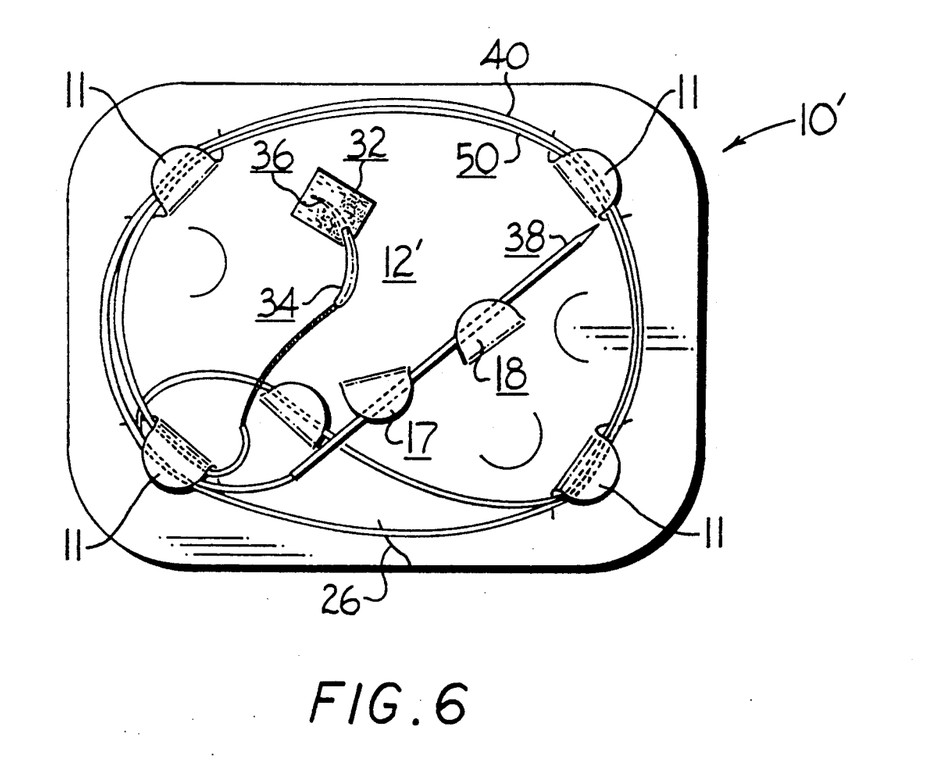
FIG. 6 is a plan view of the base panel of another embodiment of the suture retainer of FIG. 1 in accordance with this invention loaded with a double-armed suture possessing one straight needle and one small curved needle.
Figure 7:
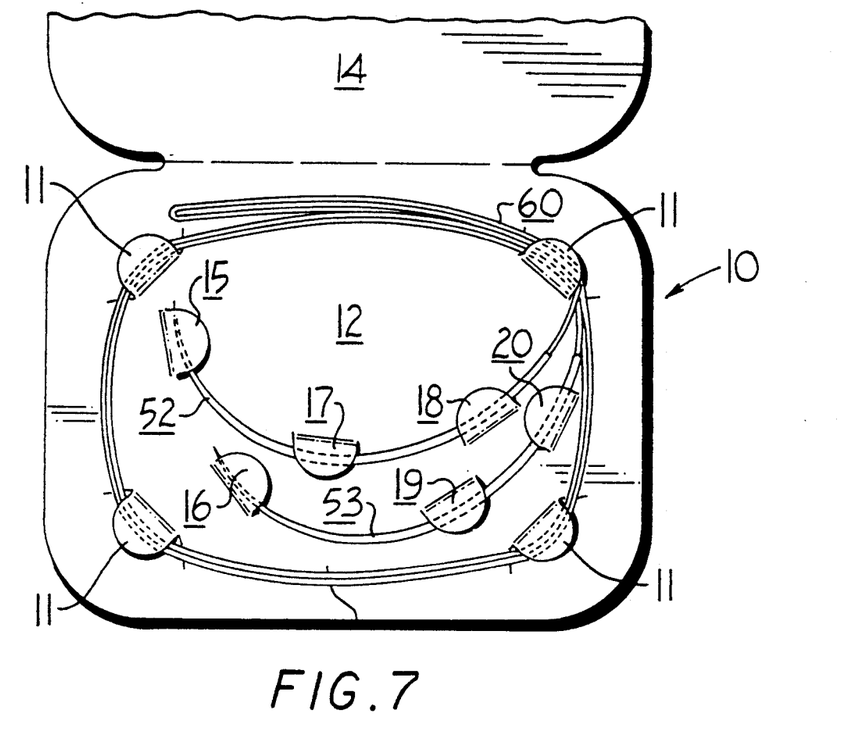
FIG. 7 is a plan view of the base panel of the suture retainer of FIG. 1 loaded with a double armed suture incorporating two curved needles.
Figure 8:
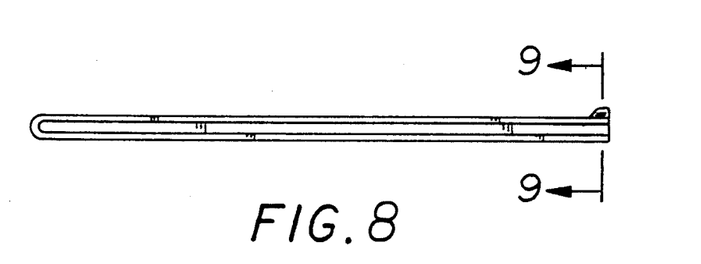
FIG. 8 is a cross sectional view of the retainer card of FIG. 3 loaded with two suture-needle assemblies.

Base panel 12 is designed to accommodate a plurality of suture/needle combinations. The sutures can be wound manually and received by the base panel in several ways. Suture retaining tabs 11 of compound configuration, e.g., the approximately W-shaped die cuts shown, are each made up of a central suture-retaining element 11a and flanking suture-retaining elements 11b and 11c oriented in a direction which is opposite that of element 11a. In the packaged condition of the suture, suture-retaining element 11a will be depressed below, or elevated above, the plane of base member 12 with flanking elements 11b and 11c being disposed outside the plane of the panel in a manner which is opposite that of element 11a. Thus, e.g., if element 11a is elevated above the plane of the panel in the packaged condition of the retainer, elements 11b and 11c will be depressed below the plane of the panel (as illustrated in FIGS. 2, 6 and 7).

Figure 10:
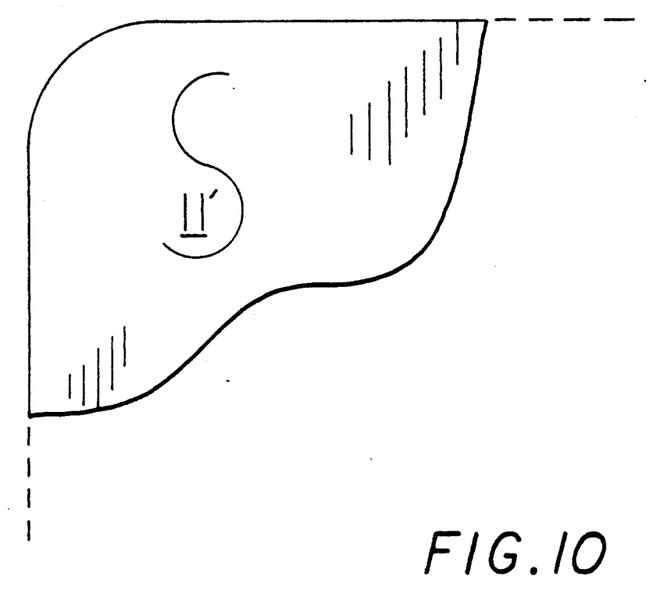
FIG. 10 is a fragmented plan view of the suture retainer of the present invention illustrating another embodiment of a suture retaining tab therewith.
Figure 11:
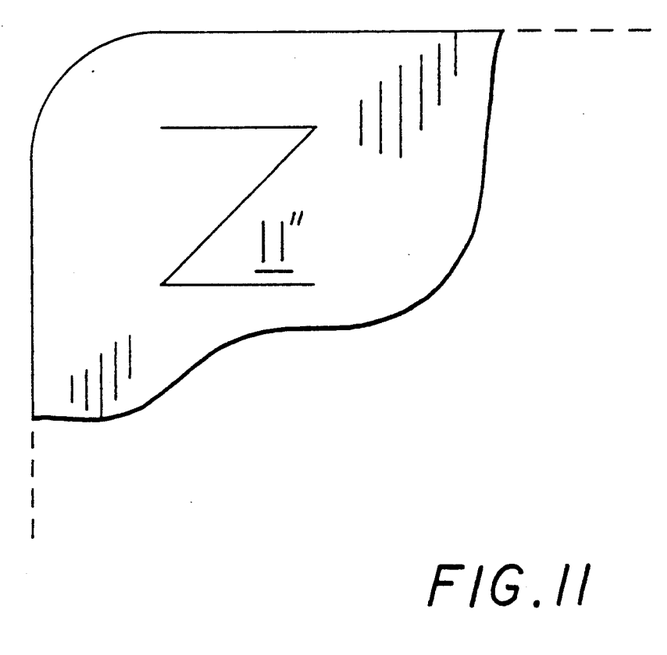
FIG. 11 is a fragmented plan view of the suture retainer of the present invention illustrating an additional embodiment of the suture retaining tab therewith.

Suture-retaining elements 11a, 11b and 11c cooperate with each other to engage the wound suture and secure it to the base panel with little if any tendency of the suture to work itself free from its engagement with these elements, a further advantage over the prior art U-shaped tab arrangement where premature disengagement of the packaged suture from its retainer is more likely to occur. Tab 11 can be oriented differently from that shown; thus, e.g., the W-shape of the tab can be rotated 180° to orient the concave edge of element 11a toward the center of base panel 12 and away from its edge, precisely the opposite of the orientation shown. Tab 11 can be given other compound configurations in addition to the W-shape shown. Thus, e.g., tab 11 can assume the shape, or approximate shape, of an "S" (11' in FIG. 10), an "N" or a "Z" (11" in FIG. 11), etc., provided it meets the defined condition of possessing at least one pair of opposed elements with one element of the pair being elevated above, and the other element of the pair being depressed below, the plane of base panel 12 in the packaged condition of retainer 10.

The number and distribution of suture retaining tabs 11 can vary. While there must be at least two of the tabs, there can be more than the four tabs shown. The tabs can be located at the corners of base panel 12 as shown or they can be arranged differently, e.g., at the midpoint of each side of base panel 12.

C-shaped needle-retaining die-cut tabs 15-20 are strategically distributed in the central region of base panel 12, advantageously in an irregular or asymmetric pattern such as that shown to accommodate any of a variety of needle sizes and configurations.

Figure 3:
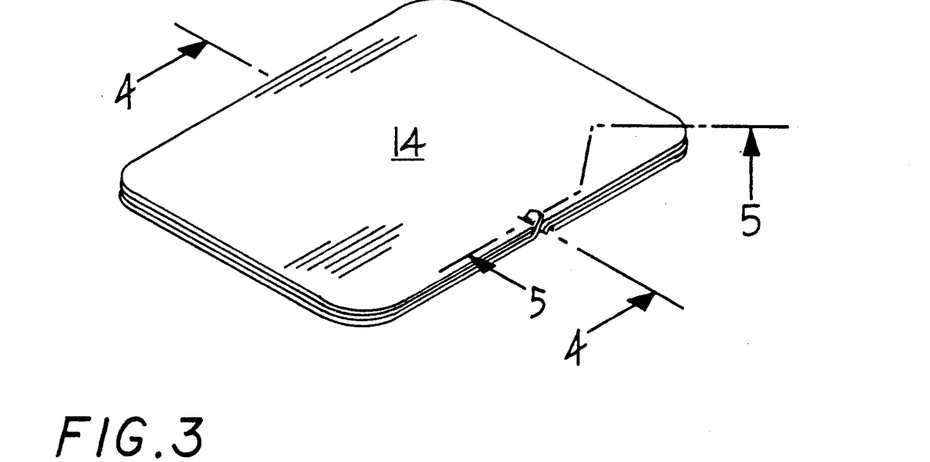
FIG. 3 is a perspective view of the loaded suture retainer of FIG. 2 shown in the fully closed and locked condition.
Figure 4:
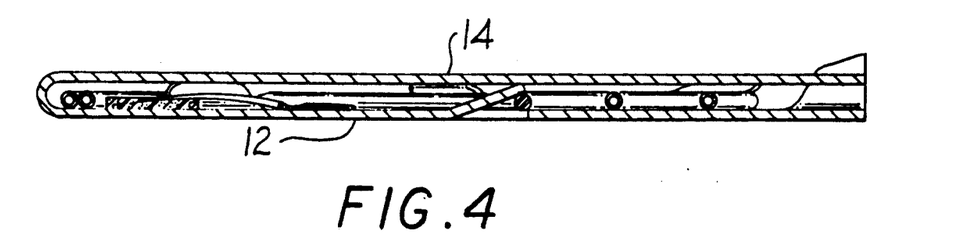
FIG. 4 is a cross sectional view of the suture retainer of FIG. 3 taken along line 4—4 thereof.
Figure 5:
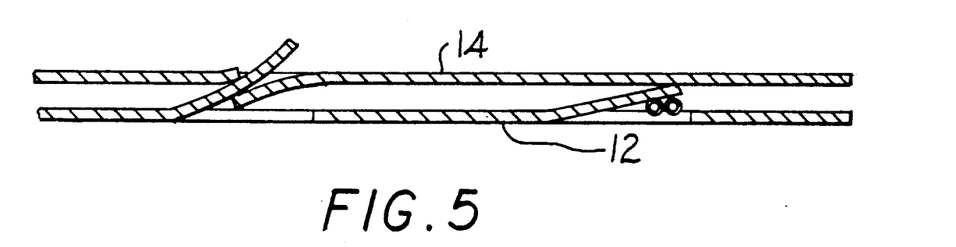
FIG. 5 is an expanded view of a sectional area of the suture retainer of FIG. 3 taken along line 5—5 thereof.
Figure 9:
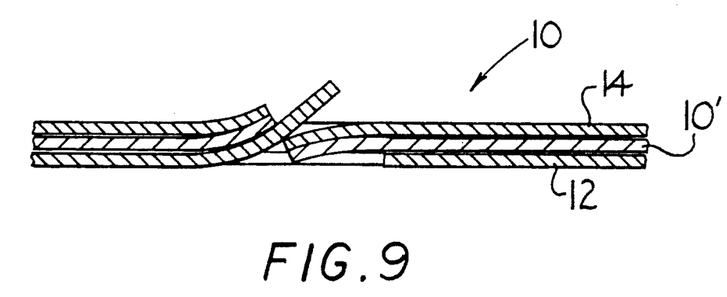
FIG. 9 is an expanded sectional view illustrating in detail the locking mechanism of the suture retainer of FIG. 3.

On folding over the cover panel 14 on base panel 12, slit 25 on cover panel 14 can be made to engage slit 26 on base panel 12 by a twisting action which locks the panels together as shown in FIG. 3. This locking engagement is illustrated in greater detail in FIGS. 4, 5 and 9. In the embodiment shown in FIG. 9, a second retainer 10' consisting solely of a base panel 12', e.g., as shown in FIG. 6, is sandwiched between base panel 12 and cover panel 14 of first retainer 10.

In the suture retainer shown in FIG. 2, suture 40 is wound about suture-retaining tabs 11, straight needle 41 being retained by needle-retaining tabs 17 and 18. The packaging arrangement of double armed suture-needle device 50 on suture retainer 10' of FIG. 6 is similar, suture 40 being wound about tabs 11, end 32 of curved needle 34 piercing polymeric foam section 36 to safely secure this needle in place and straight needle 38 being secured in place by needle retaining tabs 17 and 18. In yet another packaging arrangement, the suture component of double armed suture 60 of retainer card 10 shown in FIG. 7 is wound about tabs 11, first curved needle 52 being retained by tabs 15, 17 and 18 and second curved needle 53 being retained by tabs 16, 19 and 20.

Figure 12:
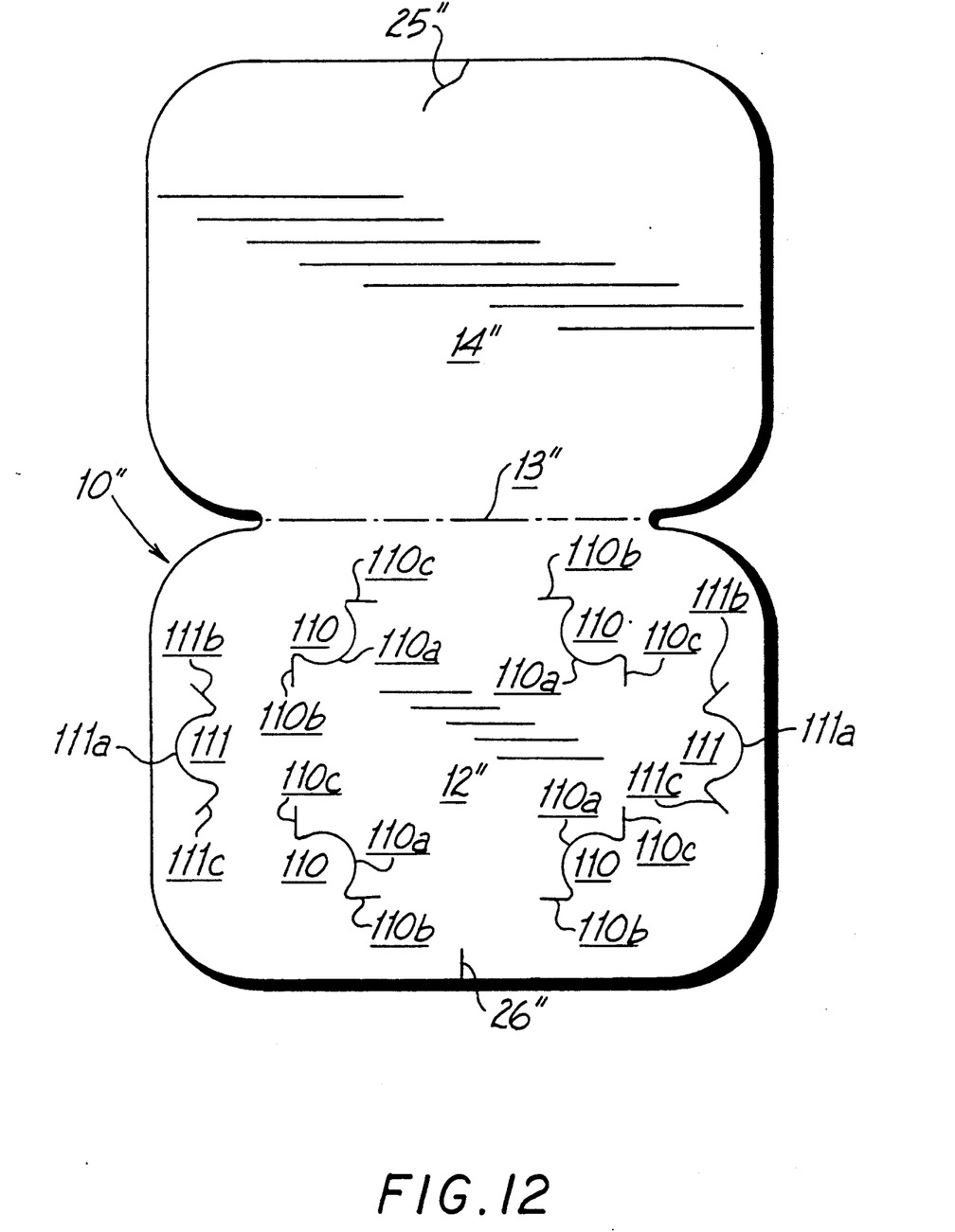
FIG. 12 is a plan view of another embodiment of a suture retainer in accordance with this invention shown in the fully open condition.
Figure 13:
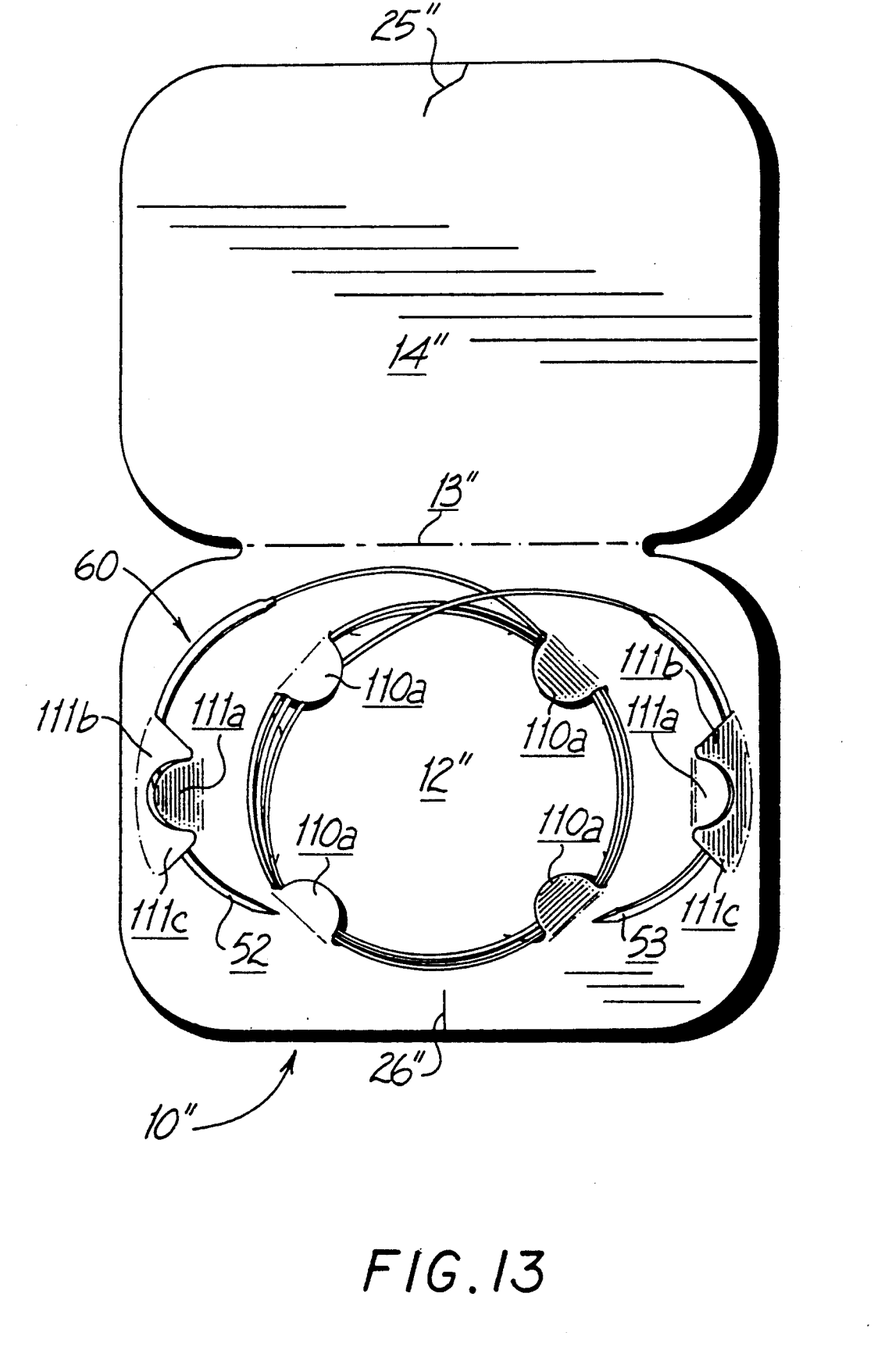
FIG. 13 is a plan view of the base panel of the suture retainer of FIG. 12 loaded with a double armed suture incorporating two curved needles.

In the suture retainer 10" shown in FIG. 12, six tabs 110 and 111 are arranged for retaining a needle and/or a suture. More explicitly, four tabs 110 are arranged in substantially regular or symmetric orientation with respect to one another, with two tabs 111 arranged outside this regular or symmetric configuration and opposite one another as shown in FIG. 12. The suture component of double armed suture 60 is wound about tabs 110, with first and second curved needles 52 and 53 being retained by tabs 111 as shown in FIG. 13. In particular, suture 60 is retained by the four tabs 110 with one element 110a elevated above the plane of base member 12" and the other flanking elements 110b and 110c depressed below the plane of base panel 12". For retaining needles 52 and 53, all elements 111a, 111b and 111c of needle-retaining tabs 111 are elevated above the plane of the base panel member 12". Depending upon orientation of suture retainer 10", elements 111a, 111b and 111c of needle-retaining tabs 111 can be considered as being depressed below the plane of the base panel member 12". Reference numerals 25' and 26' denote respective slits which engage one another by twisting action, in the same manner as slits 25 and 26 in FIGS. 1-3. Reference numeral 14" denotes a cover panel connected to base panel 12" along a foldable score line 13".

In a preferred method of loading the retainer of FIG. 12, suture 60 is wound around a substantially cylindrical mandrel. After being removed from the mandrel the suture, which is preferably a monofilament polymeric or steel suture, has a tendency to expand to its uncoiled condition. The coiled suture is placed under tabs 110a (see FIG. 13) such that the tendency of the coiled suture to expand or unwind holds the suture in place and in engagement with tabs 110a. Curved needles 52 and 53 are placed under and held in place by tabs 111. Once again, the tendency of the suture material to unwind aids in securely holding needles 52 and 53 under tabs 111.

What is claimed is:

1. A suture retainer comprising
   a base panel possessing two spaced-apart suture-engaging tabs defined thereon,
   each said suture-engaging tab comprising at least one pair of opposing elements, with one element of said pair being elevated above a plane of said base panel and said other element of said pair being depressed below said base panel plane, when said suture retainer is in packaged condition, and
   at least two spaced-apart needle-engaging tabs defined upon the base panel, the number and distribution of the needle-engaging tabs being such as to accommodate a variety of needle sizes or configurations.

2. The suture retainer of claim 1 wherein the suture-engaging tabs possess an approximately W-configuration.

3. The suture retainer of claim 1 wherein the suture-engaging tabs possess an approximately S-configuration.

4. The suture retainer of claim 1 wherein the suture-engaging tabs possess an approximately Z-configuration.

5. The suture retainer of claim 1 wherein the suture-engaging tabs each possess an approximately N-configuration.

6. The suture retainer of claim 1 wherein the base panel is of rectangular geometry and there are four suture-engaging tabs.

7. The suture retainer of claim 6 wherein the base panel is of square geometry.

8. The suture retainer of claim 6 wherein said needle-engaging tabs are disposed upon opposite sides of said base panel plane from one another.

9. The suture retainer of claim 6 wherein said four suture-engaging tabs are arranged in a symmetric pattern upon said base panel in the central region thereof.

10. The suture retainer of claim 9 wherein said two needle-engaging tabs are arranged upon said base panel outside of said symmetric pattern of said suture-engaging tabs.

11. The suture retainer of claim 1 wherein said needle-engaging tabs are each formed by a pair of opposing elements, with both said elements being elevated above or depressed below said base panel plane, when said suture retainer is in packaged condition.

12. The suture retainer of claim 11 wherein the needle-engaging tabs each possess an approximately W-configuration.

13. The suture retainer of claim 11 wherein the needle-engaging tabs each possess an approximately S-configuration.

14. The suture retainer of claim 11 wherein the needle-engaging tabs each possess and approximately Z-configuration.

15. The suture retainer of claim 11 wherein the needle-engaging tabs each possess an approximately N-configuration.

* * * * *